United States Patent [19]

Marzoni et al.

[11] Patent Number: 4,704,395

[45] Date of Patent: Nov. 3, 1987

[54] CYCLIC ETHER ESTERS OF 2-SUBSTITUTED-6-(SUBSTITUTED AND UNSUBSTITUTED) DIHYDROLYSERGIC ACID USEFUL AS 5HT RECEPTOR ANTAGONISTS

[75] Inventors: Gifford P. Marzoni; William L. Garbrecht, both of Indianapolis, Ind.

[73] Assignee: Eli Lilly and Company, Indianapolis, Ind.

[21] Appl. No.: 811,193

[22] Filed: Dec. 20, 1985

[51] Int. Cl.$^4$ ..................... A61K 31/48; C07D 457/04
[52] U.S. Cl. ...................................... 514/288; 546/67; 546/68; 546/69
[58] Field of Search ............................ 546/69, 67, 68; 514/288

[56] References Cited

U.S. PATENT DOCUMENTS

| | | | |
|---|---|---|---|
| 3,113,133 | 12/1963 | Hoffmann et al. | 260/285.5 |
| 3,183,234 | 5/1965 | Garbrecht et al. | 260/285.5 |
| 3,228,941 | 1/1966 | Bernardi et al. | 260/285.5 |
| 3,249,617 | 5/1966 | Hofmann et al. | 260/285.5 |
| 3,580,916 | 5/1971 | Garbrecht | 260/285.5 |
| 4,230,859 | 10/1980 | Rucman | 546/69 |

FOREIGN PATENT DOCUMENTS

| | | | |
|---|---|---|---|
| 2056437 | 3/1981 | European Pat. Off. | 546/67 |
| 122044 | 10/1984 | European Pat. Off. | |

OTHER PUBLICATIONS

Cohen et al., *J.P.E.T.,* 227, 327 (1983) (Cohen I).
Cohen et al., ibid, 232, 770 (1984) (Cohen II).
Lemberger et al., *Life Sci.,* 35, 71 (1984).
Cohen et al., *Drug Dev. Res.,* 5, 313 (1985) (Cohen IV).
Hingten et al., Abstract 37.4, *Soc. for Neurosci.* (13th Annual Meeting, Nov., 1983).

*Primary Examiner*—Donald G. Daus
*Assistant Examiner*—Cecilia Shen
*Attorney, Agent, or Firm*—Bruce J. Barclay; Leroy Whitaker

[57] ABSTRACT

Cyclic ether esters of 1-substituted-6-$C_{1-4}$ straight chain alkyl (or allyl)ergoline-8$\beta$-carboxylic acid, useful as 5HT receptor antagonists.

20 Claims, No Drawings

CYCLIC ETHER ESTERS OF 2-SUBSTITUTED-6-(SUBSTITUTED AND UNSUBSTITUTED) DIHYDROLYSERGIC ACID USEFUL AS 5HT RECEPTOR ANTAGONISTS

BACKGROUND OF THE INVENTION

Garbrecht, U.S. Pat. No. 3,580,916, discloses a group of lysergic (I) and 9,10-dihydrolysergic acid (II) esters formed with various open chain and cyclic diols. The following structures summarize the disclosure in Garbrecht.

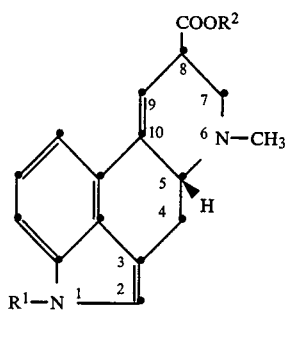

I and

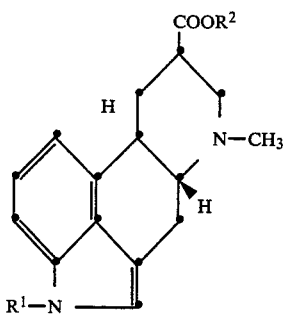

II wherein $R^1$ is H, $C_{1-3}$ alkyl, allyl or benzyl and $R^2$ is $C_2$–$C_8$ monohydroxyalkyl, $C_{2-8}$ dihydroxyalkyl or $C_{5-11}$ monohydroxycycloalkyl having from 5-8 ring carbons. The compounds are useful as serotonin antagonists, the patent stating that "In animals, the compounds act as neurosedatives . . . and are therefor useful in calming . . . animals". The use of compounds according to II, wherein $R^2$ is mono or dihydroxyalkyl, in migraine and other disease states characterized by an excess of peripheral 5HT, is disclosed in EPO No. 122,044 published 10-17-84.

The interest in the Garbrecht compounds has been intensified by the finding that they had excellent peripheral serotonin antagonist activity against 5HT$_2$ receptors and did not interact, either as agonists or antagonists, with other receptors, particularly alpha$_1$ receptors.

The most active peripheral serotonin antagonist from Garbrecht was the compound 1-isopropyl-6-methyl-8β-(1-methyl-2-hydroxy)propoxycarbonyl-5R-ergoline (II in which $R^1$ is isopropyl and $R^2$ is 1-methyl-2-hydroxypropyl). In the above name, 5R refers to the beta orientation of the C-5 hydrogen. The C-10 hydrogen is alpha—10R, and the beta orientation at C-8 is the same as in either lysergic or 9,10-dihydrolysergic acid—8R. Both of these acids have a 6-methyl group. An alternate name for the Garbrecht compound is 1-isopropyl-9,10-dihydrolysergic acid 1-methyl-2-hydroxypropyl ester.

Cohen et al. *J.P.E.T.*, 227, 327 (1983) (Cohen I) reported that the above compound, given the code number LY53857, was a potent antagonist of vascular contraction to serotonin, which effect is mediated by 5HT$_2$ receptors. The compound had minimal affinity for vascular alpha adrenergic, dopaminergic and histaminergic receptors ($K_{dissoc.} \cong 10^{-10}$ vs $\cong 10^{-5}$). Other papers on the pharmacology of LY53857 include Cohen et al., *J.P.E.T.*, 232, 770 (1985) (Cohen III), Harriet Lemberger et al., *Life Sciences*, 35, 71 (1984), Cohen, *Drug Development Res.*, 5, 313 (1985), (Cohen IV). Cohen and Fuller, EPO No. 122,044 published 10-17-84, covers the use of hydroxyalkyl esters of 1-alkyl 9,10-dihydrolysergic acid as peripheral 5HT$_2$ receptor antagonists.

Four additional examples of ergolines with a substituent on the indole nitrogen are: U.S. Pat. No. 3,113,133, Hofmann et al., which discloses and claims esters and amides carrying an indole N substituent such as a lower alkyl or alkenyl group or an aralkyl group. The compounds are said to be useful as serotonin antagonists, in treating inflammatory, arthritic and allergic diseases and in treating carcinoid syndrome.

U.S. Pat. No. 3,249,617, Hofmann et al., which covers (indole) N-alkyl or allyl lysergic acids, useful as intermediates.

U.S. Pat. No. 3,228,941, Bernardi et al., which discloses and claims a group of (indole) N-methylergolines—amides, hydroxamides and amidines. The compounds are alleged to have oxytoxic, adrenolytic, hypotensive, sedative and antienteraminic action.

U.S. Pat. No. 4,230,859 to Rucman which discloses dihydrolysergic acid carrying various $C_{1-5}$ alkyl groups on the indole nitrogen. The compounds are said to be useful intermediates.

Finally, ergolines actually used in the treatment of migraine include the amides: ergotamine, methysergide and ergonovine.

None of the above references indicate that cyclic ether esters of an N-alkylated dihydrolysergic acid would have peripheral serotonin antagonist properties.

SUMMARY OF THE INVENTION

This invention provides ergolines of the formula:

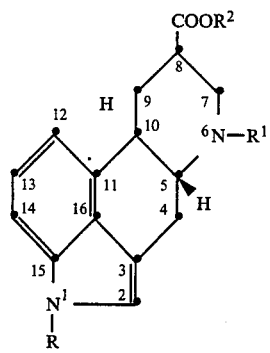

wherein R is primary or secondary $C_{1-8}$ alkyl, $C_{2-4}$ alkenyl-$CH_2$, $C_{3-8}$ cycloalkyl or $C_{3-6}$ cycloalkyl substituted $C_{1-5}$ primary or secondary alkyl, the total number of carbon atoms in R not to exceed 8; $R^1$ is allyl, H or $C_{1-4}$ straight-chain alkyl; i.e., methyl, ethyl, n-butyl, or n-propyl, and $R^2$ is

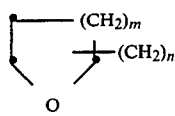

wherein n is 0-4 and m is 1 or 2 except that, when n is 0, the ester function may not be attached to the cyclic ether ring alpha to the ring oxygen; and pharmaceutically acceptable acid addition salts thereof. Compounds according to III, wherein $R^1$ is other than H, are central or peripheral serotonin $5HT_2$ receptor antagonists lacking interaction with other receptors at 5HT blocking doses. Compounds wherein $R^1$ is H are primarily intermediates.

Groups which R represents include methyl, ethyl, allyl, n-propyl, isopropyl, crotyl, methallyl, n-hexyl, sec-amyl, sec-octyl, n-heptyl, 2,4-dimethylpentyl, 2-ethylpentyl, cyclopropyl, cyclopropylmethyl, cyclopentyl methyl, 2-cyclobutyl ethyl, cyclohexyl, isobutyl, sec.-butyl, 3-methyl-2-butyl, isoamyl, 2-methylhexyl, 3-methylhexyl, 4-methylhexyl(isohexyl), 2-hexyl, 3-hexyl, n-heptyl, 2-heptyl, 3-heptyl, 4-heptyl, n-octyl, 2-octyl, 3-octyl, 4-octyl, isooctyl, 2-methylheptyl, 3-methyl-2-heptyl, and the like. Illustrative of the groups which $R^2$ represents include 4-(2-tetrahydropyranyl)butyl, 2-(3-tetrahydrofuranyl)-1-methylethyl, 3-tetrahydrofuranyl, 3-tetrahydropyranyl, 2-(2-tetrahydrofuranyl)ethyl, 4-tetrahydropyranylmethyl, 3-(4-tetrahydropyranyl)propyl, 2-methyl-3-(2-tetrahydrofuranyl)propyl, and the like.

Compounds according to the above formula are named as ergoline derivatives in which the trans(−) or 5R,10R configuration of the bridgehead hydrogens is specified (The same configuration as in the naturally-occurring 9,10-dihydro ergot alkaloids). In U.S. Pat. No. 3,580,916, a different naming system is used; the basic ring system is named as a 6aR,10aR-4,6,6a,7,8,9,10,10a-octahydroindolo[4,3-f,g]quinoline. Illustratively, by the alternate naming system, 9,10-dihydrolysergic acid becomes 6aR,10aR-7-methyl-4,6,6a,7,8,9,10,10a-octahydroindolo[4,3-f,g]quinoline-9β-carboxylic acid. Another equally valid name for 9,10-dihydrolysergic acid is 6-methyl-8β-carboxyergoline. We prefer to use the trivial name "ergoline" with the numbering system specified in III above for compounds in which $R^1$ is other than methyl and the 9,10-dihydrolysergic acid nomenclature for 6-methyl derivatives.

In addition, in 9,10-dihydrolysergic acid, the C-8 carboxyl is beta or R. Thus, again using the ergoline naming system, derivatives of 9,10-dihydrolysergic acid become derivatives of 5R,8R,10R(or 5β,8β,10α) 6-methylergoline-8β-carboxylic acid.

While the configuration at asymmetric carbons 5,8 and 10 in formula III is set (5β,8β and 10α), the cyclic ether-containing ester group ($R^2$) may contain one or more additional asymmetric carbons. For example, 1-methyl-2-(3-tetrahydrofuranyl)ethanol contains two asymmetric carbons, the β-carbon of the tetrahydrofuran ring to which the alkyl group is attached and the C-1 carbon of the alkyl chain. The ester thus exists as two racemates each containing two enantiomers or stereoisomers. This invention contemplates the use of all such optically active and racemic forms as peripheral serotonin antagonists.

Pharmaceutically-acceptable acid addition salts of the compounds of formula III include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Illustrative compounds of this invention include:
1-methyl-6-ethyl-8β-[2-(3-tetrahydropyranyl)ethyloxycarbonyl]ergoline hydrochloride
1-n-propyl-6-allyl-8β-[3-(4-tetrahydropyranyl)propyloxycarbonyl]ergoline sulfate
4-(4-tetrahydropyranyl)butyl 1-methyl-9,10-dihydrolysergate phosphate
1-isopropyl-6-n-propyl-8β-[2-(2-tetrahydrofuranyl)propyloxycarbonyl]ergoline hydrobromide
3-tetrahydropyranyl 1-n-octyl-9,10-dihydrolysergate
1-allyl-6-ethyl-8β-(2-tetrahydrofuranyl)ethyloxycarbonyl]ergoline tartrate and the like.

The preparation of compounds represented by formula III above is the general method of U.S. Pat. No. 3,580,916. According to this procedure, dihydrolysergic acid is first alkylated on the indole nitrogen using standard procedures—base plus an aliphatic halide. Liquid ammonia is a convenient solvent with sodamide as the base and an alkyl, cycloalkyl, or cycloalkyl substituted $C_{1-5}$ alkyl iodide or an alkenyl chloride or bromide as the alkylating agent. (See also U.S. Pat. No. 3,183,234, Garbrecht and Lin, which contains general directions and a specific example of the above alkylation procedure).

Alternatively, the process described in the copending application of Marzoni, Ser. No. 782,339 filed Oct. 1, 1985, can be used whereby an aryl sulfonate of the formula R—O—$SO_2$—phenyl—Y wherein Y is H, Br, $NO_2$ or $CH_3$ is used in the presence of an alkali metal hydroxide, conveniently sodium hydroxide, in an aprotic solvent such as DMSO.

With the indole nitrogen substituent in place, if 1-R-9,10-dihydrolysergic acid ($R^1$ is methyl) is the starting material, the next step in the synthetic procedure is esterification. This procedure requires relatively mild reaction conditions according to U.S. Pat. No. 3,580,916. The reaction is, however, an otherwise standard acid-catalyzed esterification. p-Toluenesulfonic acid is a useful catalyst here. The acid and the cyclic ether alkanol are the reactants and a convenient work-up of the esterification mixture involves partitioning between water and a water-immiscible solvent; $(CH_2Cl)_2$ for example.

If the final product is not a 9,10-dihydrolysergic acid ester (i.e.; not a 1-R-6-methylergoline-8β-carboxylic acid ester), but is a 6-ethyl, 6-n-propyl, 6-n-butyl, 6-allyl or the like derivative, the removal of the 6-methyl group must take place prior to the final esterification with a cyclic ether alcohol. In this procedure, we prefer to use a lower alkyl ester of a 1-R-9,10-dihydrolysergic acid as a starting material. Replacement of the 6-methyl group with ethyl, n-propyl, allyl, n-butyl, can be carried out by the procedure of Kornfeld and Bach, U.S. Pat. No. 4,166,182, whereby the 6-methyl group is reacted with cyanogen bromide to form an N-cyano derivative. The cyano group is then removed by hydrogenation using zinc dust and hydrochloric acid or preferably, with base in ethylene glycol or other suitable solvent. This latter procedure yields a product containing a free carboxyl at C-8 since the hydrolysis procedure also saponifies the lower alkyl ester group. Next, reesterification with the desired $R^2OH$ (cyclic ether alcohol) takes place followed by alkylation or allylation at N-6 using an allyl chloride or alkyl iodide in the presence of base, conveniently in DMF solution.

This procedure is graphically illustrated in Reaction Scheme 1 below.

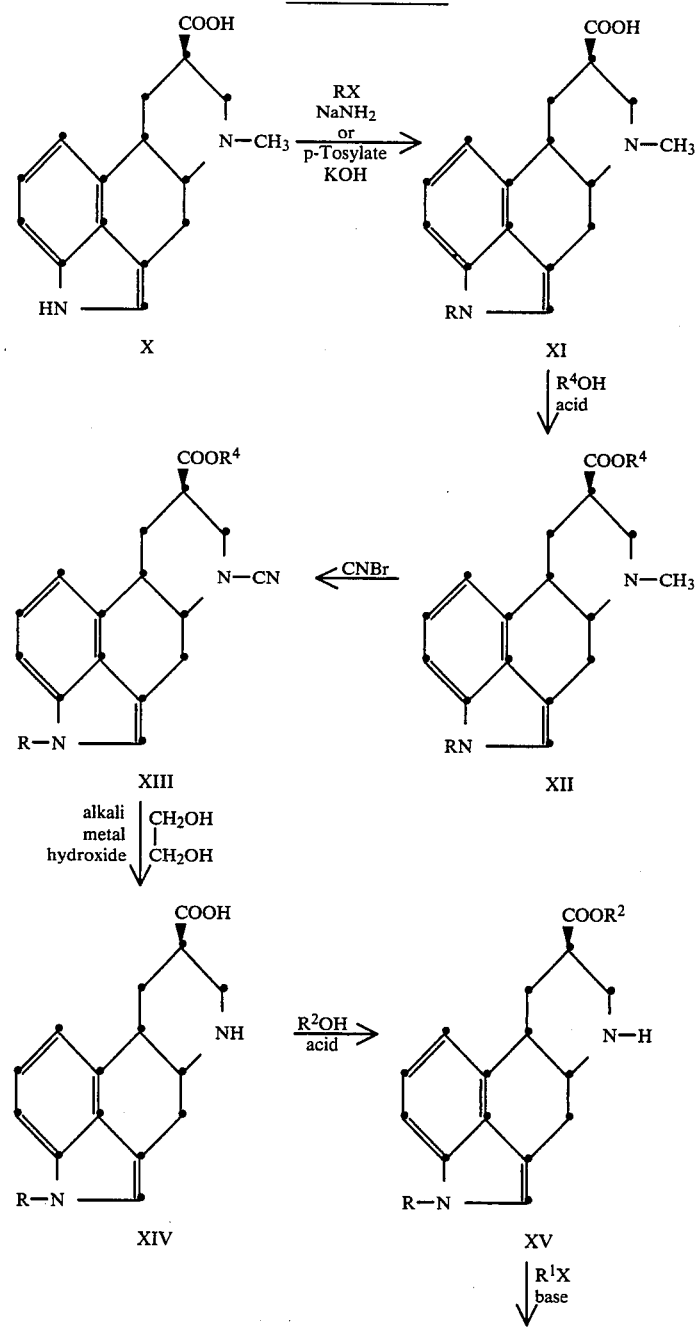

Reaction Scheme 1

Reaction Scheme 1
-continued

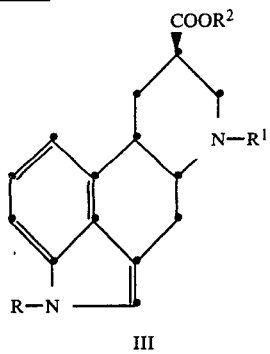

III wherein $R^4$ is $C_{1-2}$ alkyl and R, $R^1$ and $R^2$ have their previous significances.

More specifically, in the above Reaction Scheme, 9,10-dihydrolysergic acid (X) may be alkylated on the indole nitrogen with an alkyl ($C_{1-8}$ alkyl) halide a $C_{2-4}$ alkenyl-$CH_2$ halide, a $C_{3-6}$ cycloalkyl halide or a $C_{3-6}$ cycloalkyl-$C_{1-5}$ alkyl halide, (RX), using sodamide to create the reactive anion. Preferably, however, a tosylate (R—O—$SO_2$-tolyl) is employed in the presence of KOH in an aprotic solvent since this latter procedure is more generally applicable than the use of the halide, RX. The product (XI) is then esterified with a lower alkanol $R^4OH$ (a $C_{1-2}$ alkanol preferably) to yield the 1-R alkylated ester (XII). This ester is then reacted with CNBr by standard procedures to replace the methyl group with cyano (XIII). Removal of the cyano group under the preferred basic conditions yields a 1-substituted-9,10-dihydro-6-desmethyllysergic acid (XIV), since the basic conditions also saponifies the C-8 lower alkyl ester group. Next, the 1-R-6-desmethyldihydrolysergic acid is re-esterified with a desired cyclic ether alcohol to yield the 6-desmethyl ester (XV). The piperidine ring nitrogen (N-6) is then realkylated with a $C_{1-4}$ alkyl or allyl halide and base under standard conditions to yield the compounds of this invention (III).

It might seem redundant to realkylate at N-6 with a methyl group since that group is present in the 9,10-dihydrolysergic acid starting material. However, the process would enable one to insert a "tagged" ($C^{14}$ or $H^3$) methyl group for metabolic studies.

Although the above reaction sequence has been illustrated with reference to preparing cyclic ether esters, it is apparent that the procedure is readily adaptable to the provision of 1,6-dialkyl ergoline carboxylic acid esters formed with other alkanols, ether alkanols, fluoroalkanols, etc. Such process in all its ramifications is disclosed in the copending application of Whitten et al, Ser. No. 782,337 filed Oct. 1, 1985.

The following examples illustrate the preparation of compounds according to III above.

EXAMPLE 1

Preparation of 3-(2-Tetrahydrofuranyl)propyl-1-isopropyl-9,10-dihydrolysergate

A reaction mixture prepared from 2.0 g of 1-isopropyl-9,10-dihydrolysergic acid, 2.0 g of p-toluenesulfonic acid and 20.0 g of 3-tetrahydrofuranylpropanol, was heated in the range 60°–70° C. overnight. TLC ($CHCl_3/CH_3OH/HOAc$ 18:6:1) indicated no remaining unreacted acid. 100 ml of distilled water were added and the aqueous mixture made basic by the addition of 14N aqueous ammonium hydroxide. The now alkaline mixture was extracted with 100 ml of ethyl acetate. The ethyl acetate extract was in turn extracted with two 100 ml portions of water and was then dried. Evaporation of the solvent yielded 2.72 g of 3-(2-tetrahydrofuranyl)-propyl 1-isopropyl-9,10-dihydrolysergate formed in the above reaction. The free base was converted to the maleate salt with 0.86 g of maleic acid in 15 ml of ethyl acetate. 250 ml of ether were added. Crystals of the maleate salt formed. The crystallization mixture was chilled overnight at about 0° C., and was then filtered. The filter cake was washed with ether; yield of crude maleate salt=2.40 g.

The crude salt was dissolved in ethyl acetate, the solution decolorized and filtered and ether added to the filtrate until crystallization began. The mixture was chilled overnight and then filtered; yield=1.73 g. These crystals were then subjected to preparative HPLC (water C-18 1:1 acetonitrile/0.1M $NH_4OAc$). Evaporation of fractions 1–13 removed the acetonitrile solvent and the resulting aqueous phase was extracted with ethylene dichloride (two 200 ml portions). Evaporation of the solvent from the dried ethylene dichloride solution gave a 1.42 g residue comprising the free base of 3-(2-tetrahydropyranyl)propyl 1-isopropyl-9,10-dihydrolysergate (the maleate salt is converted to the free base by the ammonium acetate buffer used in preparative HPLC). The free base was reconverted to the maleate salt as before and the salt crystallized from ethyl acetate/ether. 1.06 g of crystalline maleate salt were obtained in 99% purity by HPLC (C-18 0.1 M ammonium acetate/acetonitrile 1:1); molecular ion at 424 by mass spectrum. The crystals were recrystallized from methanol/ether; yield of 3-(2-tetrahydropyranyl)propyl 1-isopropyl-9,10-dihydrolysergate maleate=0.84 g; mp=182°–183° C.

Analysis: Calc.: C, 66.65; H, 7.46; N, 5.18. Found: C, 66.81; H, 7.36; N, 5.14.

Following the above procedure, 2-tetrahydrofuranyl-methyl 1-isopropyl-9,10-dihydrolysergate maleate was prepared. The maleate salt was recrystallized twice from water and then from methanol/ether yield=0.71 g (from 2.0 g of acid); mp=181°–183° C.

Analysis: Calc.: C, 65.61; H, 7.08; N, 5.47. Found: C, 65.43; H, 6.87; N, 5.22.

Still following the above procedure, 2-tetrahydropyranylmethyl 1-isopropyl-9,10-dihydrolysergic acid maleate was prepared; crude yield of crystalline material (from ethyl acetate/ether) was 1.83 g. The crystals were subjected to preparative HPLC (C-18 1:1 acetonitrile/0.1 M ammonium acetate). Cuts 9–16 were combined and the acetonitrile removed by evaporation. The residue, comprising 2-tetrahydropyranylmethyl 1-isopropyl-9,10-dihydrolysergate free base formed during the HPLC was extracted with a 200 and a 100 ml portions of ethylene dichloride. The extracts were dried and the solvent evaporated therefrom; yield=1.22 g of free base. The maleate salt was again prepared and crystallized from ethyl acetate/ether; yield of crystalline 2-tetrahydropyranylmethyl 1-isopropyl-9,10-dihydrolysergate maleate (99.9% pure by HPLC)=1.31 g; molecular ion at 410 by mass spectrum.

Analysis: Calc.: C, 66.14; H, 7.27; N, 5.32. Found: C, 66.23; H, 7.50; N, 5.52.

Still following the above procedure 1-isopropyl-9,10-dihydrolysergic acid (1.5 g) and 4-hydroxytetrahydropyran were reacted in the presence of p-toluenesulfonic acid to give a yield (crude) of 4-tetrahydropyranyl 1-isopropyl-9,10-dihydrolysergate. The free base was converted to the maleate salt in ethyl acetate. The salt crystallized on the addition of ether; yield of crystalline maleate=1.66 g. The crystals were subjected to preparative HPLC as above. Cuts 10–16 were combined and the organic solvent removed in vacuo. The aqueous layer was extracted with ethylene dichloride. The combined extracts were dried and the solvent removed in vacuo to yield 1.14 g of 4-tetrahydropyranyl 1-isopropyl-9,10-dihydrolysergate free base. The free base was reconverted to the maleate salt as before; yield=1.16 g (98.9% pure by HPLC); molecular ion at 396 by mass spectrum.

Analysis (block dried at 120° C.): Calc.: C, 65.61; H, 7.08; N, 5.47. Found: C, 65.85; H, 6.95; N, 5.18.

This invention also provides novel methods whereby 5HT receptors are blocked. Such methods are potentially useful in treating disease states in which an excess of circulating serotonin is a major contributing cause. These disease states include hypertension, anorexia nervosa, depression, mania, thrombosis, carcinoid syndrome, migraine and vasospasm. The compounds according to III above show relatively slight affinity for other receptors, $\alpha_1$, $\alpha_2$, $\beta$, histamine, carbachol etc. and thus are highly selective in their action. Formulations in which a compound of this invention is an active ingredient also form another aspect of this invention.

In order to demonstrate that compounds according to formula III have an extremely high affinity for $5HT_2$ receptors, apparent dissociation constants ($K_B$) as a measure of affinity for $5HT_2$ receptors, expressed as the negative logarithm, have been determined according to the following protocol.

Male Wistar rats (150–300 gram weight) were killed and their external jugular veins and thoracic aortas dissected free of connective tissue, cannulated in situ and placed in a modified Krebs' bicarbonate buffer in a suitable tissue bath. Two L-shaped 30-gauge stainless-steel hypodermic needles were inserted in each cannula and the dissected vessels gently pushed onto the needles. One needle was attached with thread to a stationary glass rod and the other to the transducer. [The procedure employed was that described by Hooker, Calkins and Fleisch, *Blood Vessels*, 14, 1, (1977) for use with circular smooth muscle preparations.]

The modified Krebs' bicarbonate buffer had the following makeup: (concentrations in millimoles): sodium chloride, 118.2; potassium chloride, 4.6; calcium chloride dihydrate, 1.6; potassium dihydrogenphosphate, 1.2; magnesium sulfate, 1.2; dextrose, 10.0; sodium bicarbonate, 24.8; and water q.s. to 1000 g. The tissue baths were maintained at 37° C. and were aerated with 95% oxygen-5% $CO_2$. An initial optimum resting force of 1 and 4 g was applied to the jugular vein and aorta, respectively. Isometric contractions were recorded as changes in grams of force on a Beckman Dynograph with Statham UC-3 transducers and microscale accessory attachment. Tissues were allowed to equilibrate 1 to 2 hours before exposure to drugs. Control responses to serotonin in the jugular vein and to norepinephrine in the aorta were obtained. The vessels were then incubated with appropriate concentrations of antagonist for one hour. Responses to serotonin or to norepinephrine were then repeated in the presence of the antagonist. Contraction to serotonin was evaluated in the jugular vein since this tissue produces marked responses to serotonin in the absence of alpha receptors—see Cohen and Wiley, *J. Pharm. Exp. Ther.*, 205, 400 (1978). Alpha receptor antagonist activity was evaluated in the aorta.

Apparent antagonist dissociation constants were determined for each concentration of antagonist according to the following equation:

$$K_B = \frac{[B]}{[\text{dose ratio} - 1]}$$

wherein [B] is the concentration of the antagonist and the dose ratio is the $ED_{50}$ of the agonist in the presence of the antagonist divided by the control $ED_{50}$. These results are then expressed as the negative logarithm of $K_B$. The $-\log K_B$ values obtained for compounds of this invention are given below in Table 1.

TABLE 1

Apparent Dissociation Constants for $5HT_2$ receptors determined in the rat jugular vein.

| Compound $R^2$ | salt | $5HT_2$ $-\log K_b \pm$ S.E. |
|---|---|---|
| —CH$_2$—CH$_2$—CH$_2$-(4-tetrahydropyranyl) | maleate | 8.25 ± .12 |
| —CH$_2$-(4-tetrahydropyranyl) | maleate | 8.20 ± .40 |
| —CH$_2$-(3-tetrahydropyranyl) | maleate | 8.72 ± .14 |

TABLE 1-continued

Apparent Dissociation Constants for 5HT$_2$ receptors determined in the rat jugular vein.

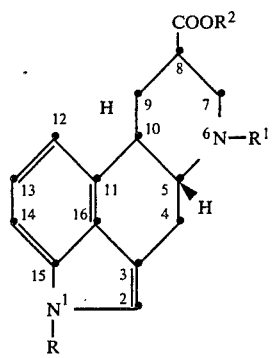

| Compound R$^2$ | salt | 5HT$_2$ −Log K$_b$ ± S.E. |
|---|---|---|
| 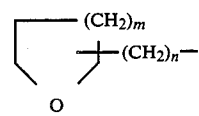 | maleate | 9.89 ± .14 |

In mammals, hypertension may be mediated through 5HT$_2$ receptors. Thus, compounds of formula III would be expected to lower blood pressure in humans as does ketanserin, another 5HT$_2$ blocker, but without the side effects attributable to alpha adrenergic receptor blockade of ketanserin.

In carrying out our novel therapeutic process, a pharmaceutically-acceptable salt of a drug according to formula III above formed with a non-toxic acid is administered orally or parenterally to a mammal with an excess of circulatory serotonin in which mammal it is desirable to block 5HT$_2$ receptors in order to alleviate symptoms attributable to excessive serotonin levels such as high blood pressure and migraine. For parenteral administration, a water soluble salt of the drug is dissolved in an isotonic salt solution and administered by the i.v. route. For oral administration, a pharmaceutically-acceptable salt of the drug is mixed with standard pharmaceutical excipients such as starch and loaded into capsules or made into tablets, each containing 0.1 to 100 mg of active drug. Dosage levels of from 0.1-10 mg/kg have been found to be effective in blocking 5HT$_2$ receptors. Thus, the oral dosage would be administered 2-4 times per day, giving a daily dosage range of about 0.003 to about 10.0 mg./kg. per day.

Other oral dosage forms, suspensions, elixirs and tablets, can also be utilized and are preparable by standard procedures.

We claim:

1. A compound of the formula:

$$\begin{array}{c} COOR^2 \\ \text{(structure with positions 2,3,4,5,6N-R}^1\text{,7,8,9,10,11,12,13,14,15,16, N}^1\text{-R)} \end{array}$$

wherein R is primary or secondary C$_{1-8}$ alkyl, C$_{2-4}$ alkenyl-CH$_2$, C$_{3-8}$ cycloalkyl or C$_{3-6}$ cycloalkyl substituted C$_{1-5}$ primary or secondary alkyl, the total number of carbon atoms in R not to exceed 8; R$^1$ is allyl, H or C$_{1-4}$ straight-chain alkyl; and R$^2$ is $$\begin{array}{c} (CH_2)_m \\ \diagdown \\ \phantom{xx}\diagup (CH_2)_n - \\ O \end{array}$$

wherein n is 0-4 and m is 1 or 2 except that, when n is 0, the ester function may not be attached to the cyclic ether ring alpha to the ring oxygen; and pharmaceutically acceptable acid addition salts thereof.

2. A compound according to claim 1 in which R is isopropyl.
3. A compound according to claim 1 in which R$^1$ is H.
4. A compound according to claim 1 in which R$^1$ is C$_{1-4}$ straight chain alkyl.
5. A compound according to claim 1 in which R$^2$ is 3-(2-tetrahydrofuranyl)propyl.
6. A compound according to claim 1 in which R$^2$ is 2-tetrahydropyranylmethyl.
7. A compound according to claim 1 in which R$^2$ is 2-tetrahydrofuranylmethyl.
8. A compound according to claim 1 in which R$^2$ is 4-tetrahydropyranyl.
9. A compound according to claim 1, said compound being 4-tetrahydropyranyl 1-isopropyl-9,10-dihydrolysergate.
10. A compound according to claim 1, said compound being 2-tetrahydrofuranylmethyl 1-isopropyl-9,10-dihydrolysergate.
11. A compound according to claim 1, said compound being 2-tetrahydropyranylmethyl 1-isopropyl-9,10-dihydrolysergate.
12. A compound according to claim 1, said compound being 3-(2-tetrahydrofuranyl)propyl 1-isopropyl-9,10-dihydrolysergate.
13. A method of blocking 5HT$_2$ receptors which comprises administering to a mammal having an excess of serotonin centrally or peripherally an 5HT$_2$ blocking dose of a compound according to claim 1.
14. A method of treating hypertension which comprises administering to a hypertensive mammal, a hypotensive dose of a compound according to claim 4.
15. A method of treating migraine which comprises administering to a mammal suffering from migraine, a migraine relieving dose of a compound according to claim 4.
16. A method of treating vasospasm which comprises administering to a mammal experiencing vasospasm, a vasospasm relieving dose of a compound according to claim 4.
17. A process according to claim 13 in which 2-tetrahydropyranylmethyl 1-isopropyl-9,10-dihydrolysergate is the drug employed.
18. A process according to claim 13 in which 2-tetrahydrofuranylmethyl 1-isopropyl-9,10-dihydrolysergate is the drug employed.
19. A process according to claim 13 in which 4-tetrahydropyranyl 1-isopropyl-9,10-dihydrolysergate is the drug employed.
20. A process according to claim 13 in which 3-(2-tetrahydrofuranyl)propyl 1-isopropyl-9,10-dihydrolysergate is the drug employed.

* * * * *